US009359617B2

(12) United States Patent
Francky et al.

(10) Patent No.: US 9,359,617 B2
(45) Date of Patent: Jun. 7, 2016

(54) MAMMALIAN EXPRESSION VECTOR

(75) Inventors: Andrej Francky, Menges (SI); Dominik Gaser, Menges (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 365 days.

(21) Appl. No.: 13/141,005

(22) PCT Filed: Dec. 18, 2009

(86) PCT No.: PCT/EP2009/067540
§ 371 (c)(1),
(2), (4) Date: Aug. 31, 2011

(87) PCT Pub. No.: WO2010/072676
PCT Pub. Date: Jul. 1, 2010

(65) Prior Publication Data
US 2011/0306090 A1    Dec. 15, 2011

(30) Foreign Application Priority Data

Dec. 22, 2008  (EP) .................................... 08172630
Apr. 17, 2009  (EP) .................................... 09158118

(51) Int. Cl.
*C12N 15/85* (2006.01)
*C12N 15/90* (2006.01)

(52) U.S. Cl.
CPC ............ *C12N 15/8509* (2013.01); *C12N 15/90* (2013.01); *A01K 2267/01* (2013.01); *C12N 2830/42* (2013.01)

(58) Field of Classification Search
None
See application file for complete search history.

(56) References Cited

U.S. PATENT DOCUMENTS

| 5,242,819 | A  | * | 9/1993 | Rajput et al. | .................. 435/359 |
| 6,524,851 | B1 | * | 2/2003 | Ellis | .............................. 435/325 |
| 2003/0040606 | A1 | * | 2/2003 | Leung | ........................ 530/387.3 |

FOREIGN PATENT DOCUMENTS

| CN | 1 390 936 | 1/2003 |
| KR | 2002 0040452 | 5/2002 |
| WO | WO 01/70949 | 9/2001 |

OTHER PUBLICATIONS

Extended European Search Report issued in European application No. EP 09 15 8118, dated Jul. 22, 2009.
Komiya et al., "Characteristics of transcription-regulatory elements for gene expression from plasmid vectors in human trophblast cell lines," *Placenta*, 27:934-938, 2006.
Melcher et al., "Plasmid vectors with a 5'-hybrid intron facilitate high-level glycoprotein expression in CHO-cells," *Biochmicia et Biophysica ACTA. Gene Structure and Expression*, 1575(1-3):49-53, 2002.
PCT International Preliminary Report on Patentability issued in International application No. PCT/EP2009/067540, dated Jun. 29, 2011.
PCT International Search Report and Written Opinion issued in International application No. PCT/EP2009/067540, dated Mar. 30, 2010.
Trill et al., "Production of monoclonal antibodies in COS and CHO cells," *Current Opinion in Biotechnology*, 6:553-560, 1995.
Xu et al., "Optimization of transcriptional regulatory elements for constructing plasmid vectors," *Gene*, 272:149-156, 2001.
Xu et al., "Strength evaluation of transcriptional regulatory elements for transgene expression by adenovirus vector," *Journal of Controlled Release*, 81:155-163, 2002.
Burchman and Berg, "Comparison of intron-dependent and intron-independent gene expression," *Molecular and Cellular Biology*, 8(10):4395-4405, 1988.
Huang and Gorman, "Intervening sequences increase efficiency of RNA 3' processing and accumulation of cytoplasmic RNA," *Nucleic Acids Research*, 18(4):937-947, 1990.
Brown, "Southern blotting and related DNA detection techniques", *Encyclopedia of Life Sciences*, 2001.
Brown, "Hybridization analysis of DNA blots", *Current Protocols in Molecular Biology*, 2.10.1-2.10.16, 1993.

\* cited by examiner

*Primary Examiner* — Catherine S Hibbert
(74) *Attorney, Agent, or Firm* — Parker Highlander PLLC

(57) ABSTRACT

The present invention describes new mammalian expression vectors comprising a novel combination of regulatory elements and one or more selection marker gene(s). The vector allows for incorporation of at least one, preferably two or more genes of interest, its/their subsequent expression, and for selection of transfected cells using, e.g., G418 and/or MTX. The pDGPΔGOI vector as an example for a mammalian expression vector according to the present invention exhibits a 9555 bp sequence, one strand of which is represented by SEQ ID NO:2.

20 Claims, 5 Drawing Sheets

SEQUENCE LISTING

```
<160> NUMBER OF SEQ ID NOS: 3

<210> SEQ ID NO 1
<211> LENGTH: 870
<212> TYPE: DNA
<213> ORGANISM: Artificial Sequence
<220> FEATURE:
<223> OTHER INFORMATION: Synthetic Sequence

<400> SEQUENCE: 1
gaacttcagg gtgagtctat gggacccttg atgtttctt tccccttctt ttctatggtt      60
aagttcatgt cataggaagg ggagaagtaa cagggtacag tttagaatgg gaaacagacg    120
aatgattgca tcagtgtgga agtctcagga tcgttttagt ttcttttatt tgctgttcat    180
aacaattgtt ttcttttgtt taattcttgc tttcttttt tttcttctcc gcaattttta    240
```

| | |
|---|---|
| ctattatact taatgcctta acattgtgta taacaaaagg aaatatctct gagatacatt | 300 |
| aagtaactta aaaaaaaact ttacacagtc tgcctagtac attactattt ggaatatatg | 360 |
| tgtgcttatt tgcatattca taatctccct actttatttt cttttatttt taattgatac | 420 |
| ataatcatta tacatattta tgggttaaag tgtaatgttt taatatgtgt acacatattg | 480 |
| accaaatcag ggtaattttg catttgtaat tttaaaaaat gctttcttct tttaatatac | 540 |
| ttttttgttt atcttatttc taatactttc cctaatctct ttctttcagg caataatga | 600 |
| tacaatgtat catgcctctt tgcaccattc taaagaataa cagtgataat ttctgggtta | 660 |
| aggcaatagc aatatttctg catataaata tttctgcata taaattgtaa ctgatgtaag | 720 |
| aggtttcata ttgctaatag cagctacaat ccagctacca ttctgctttt attttatggt | 780 |
| tgggataagg ctggattatt ctgagtccaa gctaggccct tttgctaatc atgttcatac | 840 |
| ctcttatctt cctcccacag ctcctgggca | 870 |

<210> SEQ ID NO 2
<211> LENGTH: 9555
<212> TYPE: DNA
<213> ORGANISM: Artificial Sequence
<220> FEATURE:
<223> OTHER INFORMATION: Synthetic Sequence

<400> SEQUENCE: 2

| | |
|---|---|
| aattcggatc tgcgcagcac catggcctga ataacctct gaaagaggaa cttggttagg | 60 |
| taccttctga ggcggaaaga accagctgtg gaatgtgtgt cagttagggt gtggaaagtc | 120 |
| cccaggctcc ccagcaggca gaagtatgca aagcatgcat ctcaattagt cagcaaccag | 180 |
| gtgtggaaag tccccaggct ccccagcagg cagaagtatg caaagcatgc atctcaatta | 240 |
| gtcagcaacc atagtcccgc ccctaactcc gcccatcccg cccctaactc cgcccagttc | 300 |
| cgcccattct ccgcccatg gctgactaat tttttttatt tatgcagagg ccgaggccgc | 360 |
| ctcggcctct gagctattcc agaagtagtg aggaggcttt tttggaggcc taggcttttg | 420 |
| caaaaagctt ctcgaggaac ttcagggtga gtctatggga cccttgatgt tttctttccc | 480 |
| cttctttttct atggttaagt tcatgtcata ggaaggggag aagtaacagg gtacagttta | 540 |
| gaatgggaaa cagacgaatg attgcatcag tgtggaagtc tcaggatcgt tttagtttct | 600 |
| tttatttgct gttcataaca attgttttct tttgtttaat tcttgctttc tttttttttc | 660 |
| ttctccgcaa ttttttactat tatacttaat gccttaacat tgtgtataac aaaaggaaat | 720 |
| atctctgaga tacattaagt aacttaaaaa aaaactttac acagtctgcc tagtacatta | 780 |
| ctatttggaa tatatgtgtg cttatttgca tattcataat ctccctactt tattttcttt | 840 |
| tattttaat tgatacataa tcattataca tatttatggg ttaaagtgta atgttttaat | 900 |
| atgtgtacac atattgacca aatcagggta attttgcatt tgtaattta aaaaatgctt | 960 |
| tcttcttttta atatacttttt tgtttatct tatttctaat actttccta atctctttct | 1020 |
| ttcagggcaa taatgataca atgtatcatg cctctttgca ccattctaaa gaataacagt | 1080 |
| gataatttct gggttaaggc aatagcaata tttctgcata taaatatttc tgcatataaa | 1140 |
| ttgtaactga tgtaagaggt ttcatattgc taatagcagc tacaatccag ctaccattct | 1200 |
| gcttttatttt tatggttggg ataaggctgg attattctga gtccaagcta ggccctttg | 1260 |
| ctaatcatgt tcataccctct tatcttcctc ccacagctcc tgggcagtgt ccactcccag | 1320 |
| gtccaactgc acctcggttc tatcgaaaac gcgtgtcgac ccgggcggcc gcttcccttt | 1380 |
| agtgagtcga cccgggcggc cgcttccctt tagtgagggt taatgcttcg agcagacatg | 1440 |

-continued

```
ataagataca ttgatgagtt tggacaaacc acaactagaa tgcagtgaaa aaaatgcttt      1500
atttgtgaaa tttgtgatgc tattgcttta tttgtaacca ttataagctg caataaacaa      1560
gttaacaaca acaattgcat tcattttatg tttcaggttc aggggagat gtgggaggtt       1620 ttttaaagca agtaaaacct ctacaaatgt ggtaaaatcc gataaggatc gatccgggct      1680
ggcgtaatag cgaagaggcc cgcaccgatc gcccttccca acagttgcgc agcctgaatg      1740
gcgaatggac gcgccctgta gcggcgcatt aagcgcggcg ggtgtggtgg ttacgcgcag      1800
cgtgaccgct acacttgcca gcgccctagc gcccgctcct ttcgctttct tcccttcctt      1860
tctcgccacg ttcgccggct ttccccgtca gctctaaat cggggctcc ctttagggtt       1920 ccgatttaga gctttacggc acctcgaccg caaaaaactt gatttgggtg atggttcacg      1980
atctgcgcag caccatggcc tgaaataacc tctgaaagag gaacttggtt aggtaccttc      2040
tgaggcggaa agaaccagct gtggaatgtg tgtcagttag ggtgtggaaa gtccccaggc      2100
tccccagcag gcagaagtat gcaaagcatg catctcaatt agtcagcaac caggtgtgga      2160
aagtccccag gctccccagc aggcagaagt atgcaaagca tgcatctcaa ttagtcagca      2220
accatagtcc cgcccctaac tccgcccatc ccgcccctaa ctccgcccag ttccgcccat      2280
tctccgcccc atggctgact aattttttt atttatgcag aggccgaggc cgcctcggcc       2340
tctgagctat tccagaagta gtgaggaggc ttttttggag gcctaggctt ttgcaaaaag      2400
cttctcgagg aacttcaggg tgagtctatg ggaccttga tgttttcttt cccttcttt       2460 tctatggtta agttcatgtc ataggaaggg gagaagtaac agggtacagt ttagaatggg      2520
aaacagacga atgattgcat cagtgtggaa gtctcaggat cgttttagtt tcttttattt      2580
gctgttcata acaattgttt tcttttgttt aattcttgct ttcttttttt ttcttctccg      2640 caattttac tattatactt aatgccttaa cattgtgtat aacaaaagga aatatctctg       2700
agatacatta agtaacttaa aaaaaaactt tacacagtct gcctagtaca ttactatttg      2760
gaatatatgt gtgcttattt gcatattcat aatctcccta ctttattttc ttttattttt      2820
aattgataca taatcattat acatatttat gggttaaagt gtaatgtttt aatatgtgta      2880
cacatattga ccaaatcagg gtaattttgc atttgtaatt ttaaaaatg ctttcttctt       2940 ttaatatact tttttgttta tcttatttct aatactttcc ctaatctctt tctttcaggg     3000
caataatgat acaatgtatc atgcctcttt gcaccattct aaagaataac agtgataatt      3060
tctgggttaa ggcaatagca atatttctgc atataaatat ttctgcatat aaattgtaac      3120
tgatgtaaga ggtttcatat tgctaatagc agctacaatc cagctaccat tctgctttta      3180
ttttatggtt gggataaggc tggattattc tgagtccaag ctaggccctt ttgctaatca      3240
tgttcatacc tcttatcttc ctcccacagc tcctgggcag tgtccactcc caggtccaac      3300
tgcacctcgg ttctatcgaa aggcgcgtac tagtcatatg ggcgcgccgg gcggccgctt      3360 cccttagtg agggttaatg cttcgagcag acatgataag atacattgat gagtttggac       3420
aaaccacaac tagaatgcag tgaaaaaaat gctttatttg tgaaatttgt gatgctattg      3480
ctttatttgt aaccattata agctgcaata acaagttaa caacaacaat tgcattcatt       3540
ttatgtttca ggttcagggg gagatgtggg aggttttttta aagcaagtaa aacctctaca      3600
aatgtggtaa atccgataa ggatcgatcc gggctggcgt aatagcgaag aggcccgcac       3660
cgatcgccct tccaacagt tgcgcagcct gaatggcgaa tggacgcgcc ctgtagcgg       3720 gcattaagcg cggcgggtgt ggtggttacg cgcagcgtga ccgctacact tgccagcgcc      3780
```

-continued

```
ctagcgcccg ctcctttcgc tttcttccct tcctttctcg ccacgttcgc cggctttccc    3840
cgtcaagctc taaatcgggg gctccctttg gggttccgat ttagagcttt acggcacctc    3900
gaccgcaaaa aacttgattt gggtgatggt tcacgtagtg ggccatcgcc ctgatagacg    3960
gtttttcgcc ctttgacgtt ggagtccacg ttctttaata gtggactctt gttccaaact    4020
ggaacaacac tcaaccctat ctcggtctat tcttttgatt tataagggat tttgccgatt    4080
tcggcctatt ggttaaaaaa tgagctgatt taacaaatat ttaacgcgaa ttttaacaaa    4140
atattaacgt ttacaatttc gcctgatgcg gtattttctc cttacgcatc tgtgcggtat    4200
ttcacaccgc atacgcggat ctgcgcagca ccatggcctg aaataacctc tgaaagagga    4260
acttggttag gtaccttctg aggcggaaag aaccagctgt ggaatgtgtg tcagttaggg    4320
tgtggaaagt ccccaggctc cccagcaggc agaagtatgc aaagcatgca tctcaattag    4380
tcagcaacca ggtgtggaaa gtccccaggc tccccagcag gcagaagtat gcaaagcatg    4440
catctcaatt agtcagcaac catagtcccg cccctaactc cgcccatccc gcccctaact    4500
ccgcccagtt ccgcccattc tccgcccat ggctgactaa ttttttttat ttatgcagag    4560
gccgaggccg cctcggcctc tgagctattc cagaagtagt gaggaggctt ttttggaggc    4620
ctaggctttt gcaaaaagct tgattcttct gacacaacag tctcgaactt aaggctagag    4680
ccaccatgat tgaacaagat ggattgcacg caggttctcc ggccgcttgg gtggagaggc    4740
tattcggcta tgactgggca caacagacaa tcggctgctc tgatgccgcc gtgttccggc    4800
tgtcagcgca ggggcgcccg gttcttttg tcaagaccga cctgtccggt gccctgaatg    4860
aactgcagga cgaggcagcg cggctatcgt ggctggccac gacgggcgtt ccttgcgcag    4920
ctgtgctcga cgttgtcact gaagcgggaa gggactggct gctattgggc gaagtgccgg    4980
ggcaggatct cctgtcatct caccttgctc ctgccgagaa agtatccatc atggctgatg    5040
caatgcggcg gctgcatacg cttgatccgg ctacctgccc attcgaccac caagcgaaac    5100
atcgcatcga gcgagcacgt actcggatgg aagccggtct tgtcgatcag gatgatctgg    5160
acgaagagca tcaggggctc gcgccagccg aactgttcgc caggctcaag gcgcgcatgc    5220
ccgacggcga ggatctcgtc gtgacccatg gcgatgcctg cttgccgaat atcatggtgg    5280
aaaatggccg cttttctgga ttcatcgact gtggccggct gggtgtggcg gaccgctatc    5340
aggacatagc gttggctacc cgtgatattg ctgaagagct tggcggcgaa tgggctgacc    5400
gcttcctcgt gctttacggt atcgccgctc ccgattcgca gcgcatcgcc ttctatcgcc    5460
ttcttgacga gttcttctga gcgggactct ggggttcgaa atgaccgacc aagcgacgcc    5520
caacctgcca tcacgatggc cgcaataaaa tatctttatt ttcattacat ctgtgtgttg    5580
gttttttgtg tgaatcgata gcgataagga tccgcgtatg gtgcactctc agtacaatct    5640
gctctgatgc cgcatagtta agccagcccc gacacccgcc aacacccgct gacgcgccct    5700
gacgggcttg tctgctcccg gcatccgctt acagacaagc tgtgaccgtc tccgggagct    5760
gcatgtgtca gaggttttca ccgtcatcac cgaaacgcgc gagacgaaag gcctcgtga    5820
tacgcctatt tttataggtt aatgtcatga taataatggt ttcttagacg tcaggtggca    5880
cttttcgggg aaatgtgcgc ggaaccccta tttgtttatt tttctaaata cattcaaata    5940
tgtatccgct catgagacaa taaccctgat aaatgcttca ataatattga aaaggaaga    6000
gtatgagtat tcaacatttc cgtgtcgccc ttattccctt ttttgcggca ttttgccttc    6060
ctgttttgc tcacccagaa acgctggtga agtaaaaga tgctgaagat cagttgggtg    6120
cacgagtggg ttacatcgaa ctggatctca acagcggtaa gatccttgag agttttcgcc    6180
```

```
ccgaagaacg tttttccaatg atgagcactt ttaaagttct gctatgtggc gcggtattat    6240
cccgtattga cgccgggcaa gagcaactcg gtcgccgcat acactattct cagaatgact    6300
tggttgagta ctcaccagtc acagaaaagc atcttacgga tggcatgaca gtaagagaat    6360
tatgcagtgc tgccataacc atgagtgata acactgcggc caacttactt ctgacaacga    6420
tcggaggacc gaaggagcta accgcttttt tgcacaacat gggggatcat gtaactcgcc    6480
ttgatcgttg ggaaccggag ctgaatgaag ccataccaaa cgacgagcgt gacaccacga    6540
tgcctgtagc aatggcaaca acgttgcgca aactattaac tggcgaacta cttactctag    6600
cttcccggca acaattaata gactggatgg aggcggataa agttgcagga ccacttctgc    6660
gctcggccct tccggctggc tggtttattg ctgataaatc tggagccggt gagcgtgggt    6720
ctcgcggtat cattgcagca ctggggccag atggtaagcc ctcccgtatc gtagttatct    6780
acacgacggg gagtcaggca actatggatg aacgaaatag acagatcgct gagataggtg    6840
cctcactgat taagcattgg taactgtcag accaagttta ctcatatata ctttagattg    6900
atttaaaact tcatttttaa tttaaaagga tctaggtgaa gatcctttt  gataatctca    6960 tgaccaaaat cccttaacgt gagttttcgt tccactgagc gtcagacccc gtagaaaaga    7020
tcaaaggatc ttcttgagat cctttttttc tgcgcgtaat ctgctgcttg caaacaaaaa    7080
aaccaccgct accagcggtg gtttgtttgc cggatcaaga gctaccaact ctttttccga    7140
aggtaactgg cttcagcaga gcgcagatac caaatactgt ccttctagtg tagccgtagt    7200
taggccacca cttcaagaac tctgtagcac cgcctacata cctcgctctg ctaatcctgt    7260
taccagtggc tgctgccagt ggcgataagt cgtgtcttac cgggttggac tcaagacgat    7320
agttaccgga taaggcgcag cggtcgggct gaacgggggg ttcgtgcaca cagcccagct    7380
tggagcgaac gacctacacc gaactgagat acctacagcg tgagctatga aaagcgcca    7440 cgcttcccga agggagaaag gcggacaggt atccggtaag cggcagggtc ggaacaggag    7500
agcgcacgag ggagcttcca gggggaaacg cctggtatct ttatagtcct gtcgggtttc    7560
gccacctctg acttgagcgt cgatttttgt gatgctcgtc aggggggcgg agcctatgga    7620
aaaacgccag caacgcggcc tttttacggt tcctggcctt ttgctggcct tttgctcaca    7680
tggctcgaca gatccattta aattttcacc gtcatcaccg aaacgcgcga ggcagctgtg    7740
gaatgtgtgt cagttagggt gtggaaagtc cccaggctcc ccagcaggca gaagtatgca    7800
aagcatgcat ctcaattagt cagcaaccag gtgtggaaag tccccaggct ccccagcagg    7860
cagaagtatg caaagcatgc atctcaatta gtcagcaacc atagtcccgc ccctaactcc    7920
gcccatcccg cccctaactc cgcccagttc cgcccattct ccgccccatg ctgactaat    7980 ttttttttatt tatgcagagg ccgaggccgc ctcggcctct gagctattcc agaagtagtg    8040
aggaggcttt tttggaggcc taggcttttg caaaaagctt tatccccgct gccatcatgg    8100
ttcgaccatt gaactgcatc gtcgccgtgt cccaagatat ggggattggc aagaacggag    8160
acctaccctg gcctccgctc aggaacgagt tcaagtactt ccaaagaatg accacaacct    8220
cttcagtgga aggtaaacag aatctggtga ttatgggtag gaaaacctgg ttctccattc    8280
ctgagaagaa tcgacctta  aaggacagaa ttaatatagt tctcagtaga gaactcaaag    8340
aaccaccacg aggagctcat tttcttgcca aaagtttgga tgatgcctta agacttattg    8400
aacaaccgga attggcaagt aaagtagaca tggtttggat agtcggaggc agttctgttt    8460
accaggaagc catgaatcaa ccaggccacc tcagactctt tgtgacaagg atcatgcagg    8520
```

| | |
|---|---:|
| aatttgaaag tgacacgttt ttcccagaaa ttgatttggg gaaatataaa cttctcccag | 8580 |
| aatacccagg cgtcctctct gaggtccagg aggaaaaagg catcaagtat aagtttgaag | 8640 |
| tctacgagaa gaaagactaa caggaagatg ctttcaagtt ctctgctccc ctcctaaagc | 8700 |
| tatgcatttt tataagacca tgggactttt gctggcttta gatctttgtg aaggaacctt | 8760 |
| acttctgtgg tgtgacataa ttggacaaac tacctacaga gatttaaagc tctaaggtaa | 8820 |
| atataaaatt tttaagtgta taatgtgtta aactactgat tctaattgtt tgtgtatttt | 8880 |
| agattccaac ctatggaact gatgaatggg agcagtggtg gaatgccttt aatgaggaaa | 8940 |
| acctgttttg ctcagaagaa atgccatcta gtgatgatga ggctactgct gactctcaac | 9000 |
| attctactcc tccaaaaaag aagagaaagg tagaagaccc caaggacttt ccttcagaat | 9060 |
| tgctaagttt tttgagtcat gctgtgttta gtaatagaac tcttgcttgc tttgctattt | 9120 |
| acaccacaaa ggaaaaagct gcactgctat acaagaaaat tatggaaaaa tattctgtaa | 9180 |
| cctttataag taggcataac agttataatc ataacatact gttttttctt actccacaca | 9240 |
| ggcatagagt gtctgctatt aataactatg ctcaaaaatt gtgtaccttt agcttttaa | 9300 |
| tttgtaaagg ggttaataag gaatatttga tgtatagtgc cttgactaga gatcataatc | 9360 |
| agccatacca catttgtaga ggttttactt gctttaaaaa acctcccaca cctcccctg | 9420 |
| aacctgaaac ataaaatgaa tgcaattgtt gttgttaact tgtttattgc agcttataat | 9480 |
| ggttacaaat aaagcaatag catcacaaat ttcacaaata aagcattttt ttcactgcat | 9540 |
| tctagttgtg gtttg | 9555 |

<210> SEQ ID NO 3
<211> LENGTH: 3830
<212> TYPE: DNA
<213> ORGANISM: Artificial Sequence
<220> FEATURE:
<223> OTHER INFORMATION: Synthetic Sequence

<400> SEQUENCE: 3

| | |
|---|---:|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatcga tgcgcagcac catgcctga | 240 |
| aataacctct gaaagaggaa cttggttagg taccttctga ggcggaaaga accagctgtg | 300 |
| gaatgtgtgt cagttagggt gtggaaagtc cccaggctcc ccagcaggca gaagtatgca | 360 |
| aagcatgcat ctcaattagt cagcaaccag gtgtggaaag tccccaggct ccccagcagg | 420 |
| cagaagtatg caaagcatgc atctcaatta gtcagcaacc atagtcccgc ccctaactcc | 480 |
| gcccatcccg cccctaactc cgcccagttc cgcccattct ccgccccatg gctgactaat | 540 |
| ttttttatt tatgcagagg ccgaggccgc ctcggcctct gagctattcc agaagtagtg | 600 |
| aggaggcttt tttggaggcc taggcttttg caaaaagctt acgcgtgaac ttcagggtga | 660 |
| gtctatggga cccttgatgt tttctttccc cttcttttct atggttaagt tcatgtcata | 720 |
| ggaaggggag aagtaacagg gtacagttta gaatgggaaa cagacgaatg attgcatcag | 780 |
| tgtggaagtc tcaggatcgt tttagtttct tttatttgct gttcataaca attgttttct | 840 |
| tttgtttaat tcttgctttc tttttttttc ttctccgcaa ttttttactat tatacttaat | 900 |
| gccttaacat tgtgtataac aaaaggaaat atctctgaga tacattaagt aacttaaaaa | 960 |
| aaaactttac acagtctgcc tagtacatta ctatttggaa tatatgtgtg cttatttgca | 1020 |

```
tattcataat ctccctactt tatttctttt tattttaat  tgatacataa tcattataca  1080
tatttatggg ttaaagtgta atgttaat    atgtgtacac atattgacca aatcagggta  1140 atttgcatt  tgtaatttta aaaaatgctt tcttcttta  atatactttt ttgtttatct  1200
tatttctaat actttcccta atctcttct  ttcagggcaa taatgataca atgtatcatg  1260
cctctttgca ccattctaaa gaataacagt gataatttct gggttaaggc aatagcaata  1320
tttctgcata taaatatttc tgcatataaa ttgtaactga tgtaagaggt ttcatattgc  1380
taatagcagc tacaatccag ctaccattct gcttttattt tatggttggg ataaggctgg  1440
attattctga gtccaagcta ggccctttg  ctaatcatgt tcatacctct tatcttcctc  1500
ccacagctcc tgggcagaat tcgggcccgg atccctcgag tctagaaact tgtttattgc  1560
agcttataat ggttacaaat aaagcaatag catcacaaat tcacaaata  aagcattttt  1620 ttcactgcat tctagttgtg gtttgtccaa actcatcaat gtatcttatc atgtctggtc  1680
gacttaagcc agccccgaca cccgccaaca cccgctgacg cgccctgacg ggcttgtctg  1740
ctcccggcat ccgcttacag acaagctgtg accgtctccg ggagctgcat gtgtcagagg  1800
ttttcaccgt catcaccgaa acgcgcgaga cgaaagggcc tcgtgatacg cctattttta  1860
taggttaatg tcatgataat aatggtttct tagacgtcag gtggcacttt tcggggaaat  1920
gtgcgcggaa cccctatttg tttatttttc taaatacatt caaatatgta tccgctcatg  1980
agacaataac cctgataaat gcttcaataa tattgaaaaa ggaagagtat gagtattcaa  2040
catttccgtg tcgcccttat tccctttttt gcggcatttt gccttcctgt ttttgctcac  2100
ccagaaacgc tggtgaaagt aaaagatgct gaagatcagt tgggtgcacg agtgggttac  2160
atcgaactgg atctcaacag cggtaagatc cttgagagtt ttcgccccga gaacgttt   2220 ccaatgatga gcacttttaa agttctgcta tgtggcgcgg tattatcccg tattgacgcc  2280
gggcaagagc aactcggtcg ccgcatacac tattctcaga atgacttggt tgagtactca  2340
ccagtcacag aaaagcatct tacggatggc atgacagtaa gagaattatg cagtgctgcc  2400
ataaccatga gtgataacac tgcggccaac ttacttctga caacgatcgg aggaccgaag  2460
gagctaaccg cttttttgca caacatgggg gatcatgtaa ctcgccttga tcgttgggaa  2520
ccggagctga atgaagccat accaaacgac gagcgtgaca ccacgatgcc tgtagcaatg  2580
gcaacaacgt tgcgcaaact attaactggc gaactactta ctctagcttc ccggcaacaa  2640
ttaatagact ggatggaggc ggataaagtt gcaggaccac ttctgcgctc ggcccttccg  2700
gctggctggt ttattgctga taaatctgga gccggtgagc gtgggtctcg cggtatcatt  2760
gcagcactgg ggccagatgg taagccctcc cgtatcgtag ttatctacac gacggggagt  2820
caggcaacta tggatgaacg aaatagacag atcgctgaga taggtgcctc actgattaag  2880
cattggtaac tgtcagacca agtttactca tatatacttt agattgattt aaaacttcat  2940
ttttaattta aaaggatcta ggtgaagatc ctttttgata atctcatgac caaaatccct  3000
taacgtgagt tttcgttcca ctgagcgtca gaccccgtag aaaagatcaa aggatcttct  3060
tgagatcctt ttttctgcg  cgtaatctgc tgcttgcaaa caaaaaaacc accgctacca  3120
gcggtggttt gtttgccgga tcaagagcta ccaactcttt ttccgaaggt aactggcttc  3180
agcagagcgc agataccaaa tactgttctt ctagtgtagc cgtagttagg ccaccacttc  3240
aagaactctg tagcaccgcc tacatacctc gctctgctaa tcctgttacc agtggctgct  3300
gccagtggcg ataagtcgtg tcttaccggg ttggactcaa gacgatagtt accggataag  3360
```

-continued

```
gcgcagcggt cgggctgaac gggggttcg tgcacacagc ccagcttgga gcgaacgacc    3420
tacaccgaac tgagatacct acagcgtgag ctatgagaaa gcgccacgct tcccgaaggg    3480
agaaaggcgg acaggtatcc ggtaagcggc agggtcggaa caggagagcg cacgagggag    3540
cttccagggg gaaacgcctg gtatctttat agtcctgtcg ggtttcgcca cctctgactt    3600
gagcgtcgat ttttgtgatg ctcgtcaggg gggcggagcc tatggaaaaa cgccagcaac    3660
gcggcctttt tacggttcct ggccttttgc tggccttttg ctcacatgtt ctttcctgcg    3720
ttatcccctg attctgtgga taaccgtatt accgcctttg agtgagctga taccgctcgc    3780
cgcagccgaa cgaccgagcg cagcgagtca gtgagcgagg aagcggaaga                3830
```

MAMMALIAN EXPRESSION VECTOR

Figure 1:
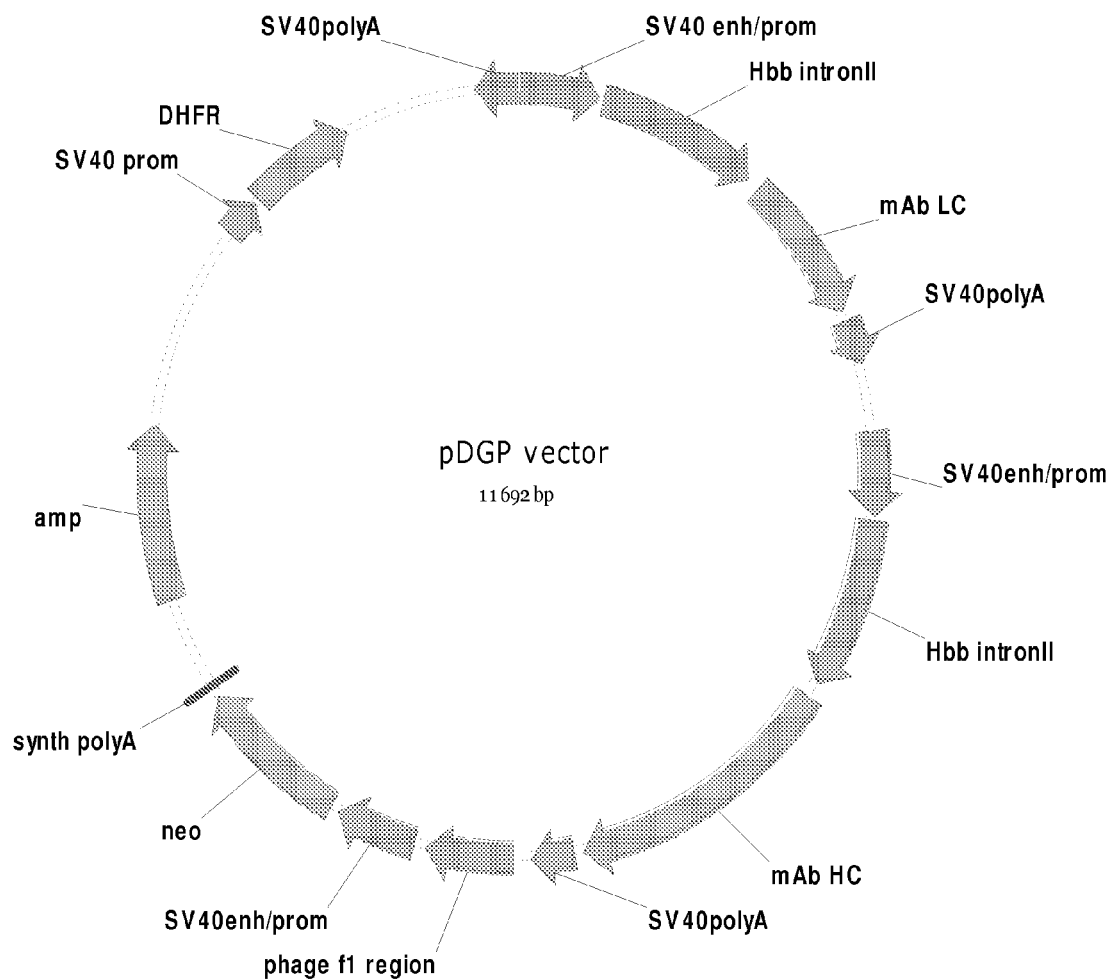

This application is a national phase application under 35 U.S.C. §371 of International Patent Application No. PCT/EP2009/067540 filed Dec. 18 2009 which claims priority to European Patent Application Nos. EP09158118.1 filed Apr. 17, 2009 and EP 08172630.9 filed Dec. 22, 2008. The entire text of the above-referenced disclosures are specifically incorporated herein by reference without disclaimer.

The present invention describes new mammalian expression vectors (with or without gene(s) of interest, GOI) for integration into the mammalian genome, the vectors comprising a novel combination of regulatory elements. In particular, the present invention describes expression vectors comprising the following regulatory elements: the simian virus 40 enhancer and early promoter region and the Hbb intronII, or fragments, derivatives and modifications thereof, wherein the expression vector is capable to take up at least one gene of interest and enable its/their expression. Preferably, such expression vector comprises at least one selection marker gene (e.g., pDGP including gene(s) of interest, see FIG. 1; e.g., pDGPΔGOI without gene(s) of interest). The vector (without gene(s) of interest) allows for incorporation of at least one, preferably two or more genes of interest, its/their subsequent expression, and for selection of transfected cells using, e.g., geneticin (G418) and/or methotrexate (MTX). The pDGPΔGOI vector as an example for a mammalian expression vector according to the present invention exhibits a 9555 bp sequence, one strand of which is represented by SEQ ID NO:2. The pDGP-AΔGOI vector as another example for a mammalian expression vector according to the present invention exhibits a 3830 bp sequence, one strand of which is represented by SEQ ID NO:3.

Currently many successive selection steps on a large number of cell pools have to be performed to generate and screen for a high producing cell pool before cell cloning. As a result, cell line development is a time-consuming and work-intensive activity.

There is a vast number of publications addressing the influence of regulatory elements on expression levels.

The positive effect of different intron sequences positioned in or just before the GOI coding sequence has been known for a long time and described in many publications (2, 4, 5, 6). Studies addressing transcriptional efficiency of different promoters were conducted identifying the CMV promoter as the most efficient (2, 3, 4, 5, 6). For this reason the GOI expression cassettes in most mammalian expression vectors today are driven by a CMV promoter and have an intron sequence just upstream of the GOI coding sequence.

Concerning the combination of GOI expression cassettes and selection marker genes in a particular expression vector, several combinations were reported and functionally tested (1). For monoclonal antibody (mAb) expression, solutions with two vectors expressing separately the light chain and heavy chain were described as well as vectors harbouring expression cassettes for both mAb chains together with the neo and dhfr expression cassettes on the same plasmid (1). In most cases only transient expression levels using intracellular reporter proteins like luciferase (2, 5, 6) were determined. By this approach it is hard to predict how a regulatory element and/or vector after integration into a chromosome will influence stable expression levels of a secreted protein, where the final expression level is the result of a complex interplay between transcription, translation, intracellular trafficking, and secretion rates. Although most important for the biopharmaceutical industry, this question is rarely addressed in the literature (3). In particular, it would seem that the relevance of a specific combination of regulatory elements and selection markers for the time needed to develop a cell line and the efficiency of cell line development has never been addressed. Consequently, the principal object of the present invention was to look for a combination of regulatory elements and selection markers superior to those known in the art in terms of the above mentioned parameters time and efficiency.

Figure 3:
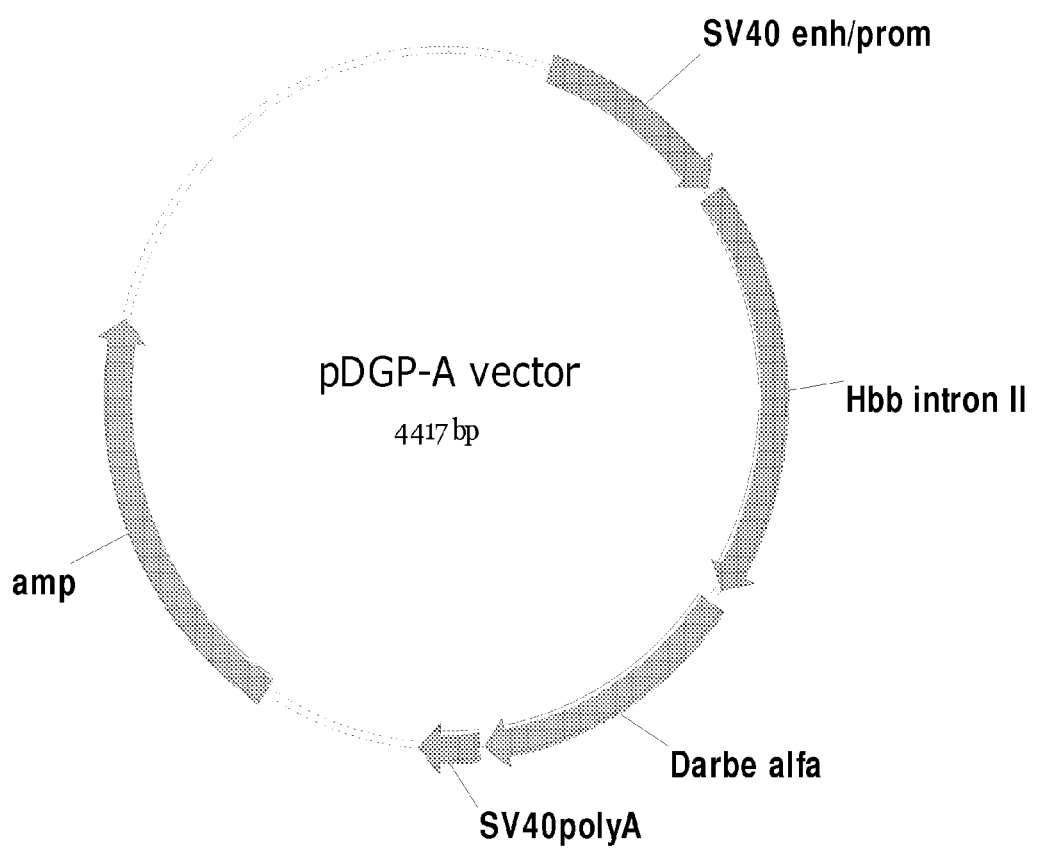

Accordingly, the present invention overcomes the downside described above and provides mammalian expression vectors for integration into the respective mammalian genome (in particular the vectors, if devoid of gene(s) of interest, designated pDGPΔGOI exhibiting the sequence of SEQ ID NO:2 and pDGP-AΔGOI exhibiting the sequence of SEQ ID NO:3; and the vectors designated pDGP and pDGP-A, if including the gene(s) of interest, see FIGS. 1 and 3, respectively) comprising a novel combination of regulatory elements: the simian virus 40 (SV40) enhancer and early promoter region, Hbb intronII, or fragments, derivatives and modifications of that intron (which is distinct from and hence must not be confused with the chimeric intron described in the literature, e.g., Xu et al. (2)), and optionally at least one selection marker gene (e.g., neo, dhfr). Such expression vectors are suitable to take up at least one gene of interest and, if so, enable its/their expression and subsequent selection of transfected cells using at least one suitable selection agent (e.g., G418 and/or MTX). Even one step-selection with G418 selects for cells expressing the at least one polypeptide encoded by the at least one gene of interest in high amounts and in a highly reproducible manner, thereby reducing the time to develop cell lines and work load significantly.

As a side note, the following should be taken into account: Expression vectors integrating into the genome that are known in the prior art upon two or more selection steps (one of which is usually MTX selection) regularly generate cells that harbour several copies of the GOI integrated into their genome and therefore express the GOI at an increased rate. Quite conversely, the expression vectors of the present invention do not require multiple copies thereof to be integrated into the genome and/or two or more rounds of selection steps in order to allow the mammalian host cell to express the GOI at an increased rate. This is the immediate outcome of the combination of the regulatory elements according to the present invention and resides in increased expression rates irrespective of the number of gene copies integrated into the genome. The advantage of the present invention is thus that there is no need to perform at least one selection step each with G418 and MTX in order to accomplish satisfactory expression rates but that only one selection step either with G418 or MTX, to mention exemplary selection systems, is sufficient.

The term "Hbb intronII" as used herein relates to any nucleic acid molecule exhibiting a sequence of the second intron of the human β-globin (hbb) gene (Hbb intron 2) including 10 bp of the sequence immediately upstream of said Hbb intron 2 in the hbb gene and 10 bp of the sequence immediately downstream of the Hbb intron 2 in the hbb gene. According to the present invention, the term "fragments, derivatives, and modifications of Hbb intronII" encompasses nucleic acid molecules which are capable of hybridising to Hbb intronII under stringent hybridisation conditions and have the same expression enhancing activity (when combined with the SV 40 enhancer and early promoter region) as has the Hbb intronII in that SV 40 enhancer/promoter combination. In particular, the term "fragments, derivatives, and modifications of Hbb intronII" encompasses nucleic acid molecules which hybridise to the strand of a nucleic acid molecule exhibiting the sequence of SEQ ID NO:1, or to its complement, or parts thereof, under stringent hybridisation conditions and which have the same expression enhancing activity as the nucleic acid molecule exhibiting the sequence of SEQ ID NO:1 in the same SV 40 enhancer/promoter combination. According to a preferred embodiment of the present invention, the Hbb intronII exhibits the sequence set out in SEQ ID NO:1.

It is well known in the art how to perform hybridisation experiments with nucleic acid molecules, i.e., the person skilled in the art knows what hybridisation conditions s/he has to use in accordance with the present invention. Such hybridisation conditions are referred to in standard text books such as *Molecular Cloning A Laboratory Manual* (Sambrook J., Russell D. W.) Cold Spring Harbor Laboratory (2001) N.Y., *Current Protocols in Molecular Biology* (eds.: Ausubel F. M., Brent R., Kingston R. E., Moore D. D., Seidman J. G, Smith J. A., Struhl K.) [Core publication in 1987—quarterly updated] Copyright© 2007 by John Wiley and Sons, Inc.

"Stringent hybridisation conditions" refer, e.g., to an overnight incubation at 40-60° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 mg/ml denatured, sheared salmon sperm DNA, followed by washing the filters in 0.1× SSC at about 65° C. Also contemplated are nucleic acid molecules that hybridise to the nucleic acid molecule exhibiting the sequence of SEQ ID NO:1, or to its complement, or parts thereof, at lower stringency hybridisation conditions. Changes in the stringency of hybridisation and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 mg/ml denatured, sheared salmon sperm DNA; followed by washes at 50° C. with 1×SSPE, 0.1% SDS. In addition to achieve even lower stringency, washes performed following stringent hybridisation can be done at higher salt concentrations (e.g., 5×SSC). It is of note that variations in the above conditions may be accomplished through the inclusion and/or substitution of alternate blocking reagents used to suppress background in hybridisation experiments. Typical blocking reagents include Denhardt's reagent, BLOTTO, heparin, denatured salmon sperm DNA, and commercially available proprietary formulations. The inclusion of specific blocking reagents may require modification of the hybridisation conditions described above, due to problems with compatibility.

Thus, a first aspect of the present invention includes the provision of an expression vector for integration into the mammalian genome, said expression vector comprising the following regulatory elements: the simian virus 40 (SV40) enhancer and early promoter region and the Hbb intronII, or fragments, derivatives and modifications thereof, and preferably the intron exhibiting the sequence of SEQ ID NO:1, wherein the expression vector is capable to take up at least one gene of interest and enable its/their expression.

Preferred embodiments of that aspect of the present invention are (i) a vector of the first aspect of the present invention, wherein the vector comprises at least one gene encoding a eukaryotic and/or prokaryotic selection marker, in particular the neomycin phosphotransferase gene (neo) from Tn5 and/or the dihydrofolate reductase (dhfr) gene;

(ii) a vector of the first aspect of the present invention, wherein the vector is circular;

(iii) a vector of the first aspect of the present invention, wherein the vector comprises at least one gene of interest under the control of said regulatory elements;

(iv) a vector of the first aspect of the present invention, wherein the at least one gene of interest is the gene encoding the light chain of an immunoglobulin and/or the gene encoding the heavy chain of an immunoglobulin;

(v) a vector of the first aspect of the present invention, wherein the order of the regulatory elements, the genes of interest, and the genes encoding a selection marker is as follows: 5'-SV40 enhancer/early promoter region, Hbb intronII, or fragments, derivatives and modifications thereof, gene encoding the light chain of an immunoglobulin, SV40 polyadenylation signal sequence; SV40 enhancer/early promoter region, Hbb intronII, or fragments, derivatives and modifications thereof, gene encoding the heavy chain of an immunoglobulin, SV40 polyadenylation signal sequence; SV40 enhancer/early promoter region, Tn5 neomycin phosphotransferase gene, a synthetic polyadenylation signal sequence, SV40 early promoter without enhancer sequence, dihydrofolate reductase gene, SV40 polyadenylation signal sequence-3';

(vi) a vector of the first aspect of the present invention, wherein the vector comprises at least one prokaryotic selection marker gene, e.g., an antibiotic resistance gene such as the ampicillin resistance gene, and/or further regulatory elements known by the skilled artisan to be advantageously included into a mammalian expression vector; and (vii) a vector of the first aspect of the present invention, wherein the vector is the pDGPΔGOI vector exhibiting a 9555 bp sequence, one strand of which is represented by the sequence of SEQ ID NO:2.

A second aspect of the present invention is a method for producing an expression vector of the first aspect of the present invention, wherein said method comprises the step of arranging the following regulatory genetic elements (a) and (b) in a vector comprising further elements commonly required for the expression vector to be functional and to integrate into the mammalian host genome: (a) the simian virus 40 enhancer and early promoter region and (b) the Hbb intronII, or fragments, derivatives and modifications thereof.

A preferred embodiment of that second aspect of the present invention is a method further comprising the step of arranging (c) at least one gene of interest such as to enable the vector to confer its/their expression and/or (d) at least one selection marker gene. According to another preferred embodiment, the at least one selection marker gene is the neomycin phosphotransferase gene from Tn5 and/or the dihydrofolate reductase gene.

A third aspect of the present invention is a vector system comprising at least two vectors as defined in any of preferred embodiments (i), (ii), and (iii), wherein each of the at least two vectors comprises at least one gene of interest. Preferred is such vector system, wherein a first gene of interest located on a first vector encodes the light chain of an immunoglobulin, and a second gene of interest located on a second vector encodes the heavy chain of an immunoglobulin. Another vector system also contemplated by the present invention comprises at least two vectors, wherein a first vector is according to the first aspect of the present invention but having no eukaryotic selection marker, and wherein a second vector comprises at least one gene encoding a selection marker conferring resistance to a transfected cell.

A fourth aspect of the present invention is a mammalian cell comprising an expression vector of any of preferred embodiments (i), (ii), (iii), (iv), (v), (vi), and (vii) of the first aspect of the present invention or a vector system according to the third aspect of the present invention. Basically any mammalian cell can be used in conjunction with the present invention as long as it allows the recombinant expression of a polypeptide.

According to a preferred embodiment of that fourth aspect of the present invention such cell is a COP cell, an L cell, a C127 cell, an Sp2/0 cell, an NS-0 cell, an NS-1 cell, an NIH3T3 cell, a PC12 cell, a PC12h cell, a BHK cell, a CHO cell, a COS1 cell, a COS3 cell, a COST cell, a CV1 cell, a Vero cell, a HeLa cell, an HEK-293 cell, a PER C6 cell, or a cell derived from diploid fibroblasts, myeloma cells, and HepG2.

A fifth aspect of the present invention relates to the method for producing a cell of the fourth aspect of the present invention, the method comprising the step of providing, and preferably transfecting, a mammalian cell with an expression vector of any of preferred embodiments (i), (ii), (iii), (iv), (v), (vi), and (vii) of the first aspect of the present invention, or with a vector system according to the third aspect of the present invention.

A sixth aspect of the present invention is a method for producing at least one polypeptide of interest, wherein said method comprises the step of culturing a cell of the fourth aspect of the present invention in a cell culture medium under conditions allowing expression of said at least one polypeptide of interest.

According to a preferred embodiment of that sixth aspect of the present invention the at least one polypeptide of interest is produced by culturing a CHO cell according to the fourth aspect of the present invention. The vectors according to the present invention are particularly suitable for producing polypeptides in rodent cells such as CHO cells. According to another preferred embodiment of that sixth aspect of the present invention such method further comprises the step of isolating from the cell culture medium said at least one polypeptide of interest.

A seventh aspect of the present invention relates to the use of the Hbb intronII, or of fragments, derivatives, and modifications thereof, but preferably of the Hbb intronII exhibiting the sequence of SEQ ID NO:1, the intron preferably being in combination with the SV 40 enhancer and early promoter region, in a mammalian expression vector for the enhancement of heterologous gene expression in mammalian expression systems.

According to a preferred embodiment of the seventh aspect of the present invention such use is defined by the Hbb intronII's, its fragment's, derivative's, and modification's location between the sequence encoding the heterologous gene and the SV 40 enhancer and early promoter region driving the expression of the heterologous gene.

An eight aspect of the invention relates to the use of the vectors according to the present invention in a method of high throughput screening of proteins.

The screening (testing) of proteins, e.g., of different variants of a candidate protein, differing in their amino acid sequence is a conventional early step in the development of new therapeutic proteins (biopharmaceuticals). The purpose of this screening programme is the assessment and subsequent optimisation of molecular features such as bioactivity, immunogenicity, aggregation behaviour, expression potential, posttranslational modifications, etc. of the protein of interest tested.

Currently, in most cases the amount of protein needed to perform the above-mentioned assessment is obtained from transient protein expression in HEK (human embryonic kidney) cells, such as HEK293 cells. For, inter alia, regulatory reasons, however, CHO cells are most often used as the final production cells in case of biopharmaceuticals. Notwithstanding this discrepancy, researchers in industry and academia keep with the current approach because of the relatively high protein titres which can be obtained almost ab initio by a transient protein expression in HEK cells when compared to CHO cells, thereby avoiding the need for a lengthy selection process to obtain stably transfected CHO cells. One of the major drawbacks of this traditional approach is, however, that the screening (testing) system and the final production system make use of host cells of different origin (human vs. hamster cells). This discrepancy of screening and production system of course entails the use of different growth media, process conditions, etc. resulting in by far less—if at all—comparable (i.e., relevant) data concerning for example the prediction of aggregation behaviour, expression levels, posttranslational modifications, etc., when the protein of interest is to be expressed in the final production system. Thus, there is a need for a screening/testing system which combines the advantages of fast and high titre protein expression (as obtained, e.g., by a transient protein expression in HEK cells) with the advantage to perform the early assessment of a protein of interest which has been obtained from a protein expression system largely corresponding to the final production system. The above problem is solved by the vectors according to the present invention, because they enable the expression of high quantities of the protein of interest in stably transfected cells after a short selection time only (for example, after two weeks of selection in, e.g., G418-containing medium). Thus, the vectors of the invention can be advantageously used to express proteins of interest (e.g., different protein variants) for testing/screening purposes directly in the production system (e.g., CHO cells) and under the cell culture (e.g., medium and process) conditions which will eventually be used for producing the final biopharmaceutical. This approach eliminates, particularly in the early development phases of a multiplicity of candidate therapeutic proteins (e.g., protein variants), the significant time loss which otherwise would be associated with the generation of a stably transfected production cell line for each of said candidate proteins. Concomitantly, this new approach generates more comparable (i.e., relevant) data with regard to the prognosis of protein quality and later behaviour both during (large-scale) production as well as in preclinical and clinical studies.

Especially preferred embodiments of the invention include the following methods and uses:

A. A method for producing an expression vector of claim 1 or 2, wherein said method comprises the step of arranging regulatory elements (a) and (b) into a vector comprising further elements commonly required for a functional expression vector: (a) the simian virus 40 enhancer and early promoter region and (b) the Hbb intronII, or fragments, derivatives and modifications thereof.

B. The method of A, wherein the method further comprises the step of arranging (c) at least one gene of interest such as to enable the vector to confer its/their expression and/or (d) at least one gene encoding a selection marker.

C. The method of B, wherein the at least one selection marker gene is the neomycin phosphotransferase gene from Tn5 and/or the dihydrofolate reductase gene.

D. Use of the Hbb intronII, or of a fragment, a derivative, or a modification thereof, in combination with the simian virus 40 enhancer and early promoter region driving the expression of a heterologous gene in a mammalian expression vector for the enhancement of heterologous gene expression in mammalian expression systems.

E. Use of D, wherein the Hbb intronII exhibits the sequence of SEQ ID NO:1.

F. Use of D or E, wherein the Hbb intronII, or its fragment, derivative, or modification, is located between the sequence encoding the heterologous gene and the SV 40 enhancer and early promoter region.

The mammalian expression vectors of the present invention exhibiting two or more GOI expression cassettes are particularly useful for the expression of multimeric, in particular heteromultimeric proteins including monoclonal antibodies. Vectors of the present invention exhibiting only one GOI expression cassette can be advantageously used to express monomeric proteins such as cytokines and hormones including erythropoietic factors like darbepoetin alfa. When multimeric proteins, in particular monoclonal antibodies, are to be expressed, a vector system is also contemplated consisting of at least two vectors of the present invention, wherein a first vector comprises a first gene of interest and a second vector comprises a second gene of interest. Preferably, in said vector system, said first gene of interest located on the first vector encodes the light chain of an immunoglobulin and the second gene of interest located on the second vector encodes the heavy chain of an immunoglobulin.

The mammalian vectors according to the present invention are suitable for the (recombinant) production of monomeric and multimeric proteins, like antibodies. Generally, (recombinant) proteins that can be produced with the mammalian vectors of the invention include those comprising amino acid sequences identical to or substantially similar to all or part of one of the following proteins: an Flt3 ligand, a CD40 ligand, erythropoiesis stimulating proteins like erythropoietin (EPO), darbepoetin including darbepoetin alfa, and thrombopoietin, calcitonin, leptin, a Fas ligand, a ligand for receptor activator of NF-kappa B (RANKL), a tumour necrosis factor (TNF)-related apoptosis-inducing ligand (TRAIL), thymic stroma-derived lymphopoietin, granulocyte colony stimulating factor, granulocyte-macrophage colony stimulating factor (GM-CSF), growth factors including mast cell growth factor, stem cell growth factor, epidermal growth factor, keratinocyte growth factor, megakaryote growth and development factor, RANTES, growth hormone, insulin, insulinotropin, insulin-like growth factors, parathyroid hormone, interferons including α-interferon, β-interferon, and γ-interferon, nerve growth factor, brain-derived neurotrophic factor, synaptotagmin-like proteins (SLP1-5), neurotrophin-3"glucagon, interleukins including IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, and IL-18, colony stimulating factors, lymphotoxin-p, tumour necrosis factor (TNF), leukemia inhibitory factor, oncostatin-M, and various ligands for cell surface molecules ELK and Hek (such as the ligands for eph-related kinases or LERKS).

Further proteins that can be produced using the mammalian vectors of the invention include proteins comprising all or part of the amino acid sequence of a receptor for any of the above-mentioned proteins, an antagonist to such a receptor of any of the above-mentioned proteins, and proteins substantially similar to such receptors or antagonists.

Also, proteins that can be produced using the mammalian vectors of the invention include proteins comprising all or part of the amino acid sequences of differentiation antigens (referred to as CD proteins) or their ligands or proteins substantially similar to either of these. Examples of such antigens are differentiation antigens including CD20, CD22, CD27, CD30, CD39, CD40, and ligands thereto.

Enzymatically active proteins or their ligands can also be produced using the mammalian vectors of the invention. Examples include proteins comprising all or part of one of the following proteins, or their ligands, or proteins substantially similar to one of these: metalloproteinase-disintegrin family members, kinases, glucocerebrosidase, superoxide dismutase, tissue plasminogen activator, Factor VIII, Factor IX, apolipoprotein E, apolipoprotein A-1, globins, an IL-2 antagonist, alpha-1 antitrypsin, TNF-alpha Converting Enzyme, ligands for any of the above-mentioned enzymes, and numerous other enzymes and their ligands.

The mammalian vectors of the invention can also be used to produce chimeric proteins selected in vitro to bind to a specific target protein and modify its activity, and antibodies or portions thereof and chimeric antibodies, i.e. antibodies having human constant antibody immunoglobulin domains coupled to one or more murine variable antibody immunoglobulin domain, fragments thereof, or substantially similar proteins. The mammalian vectors of the invention may also be used to produce conjugates comprising an antibody and a cytotoxic or luminescent substance. Examples of antibodies, in vitro-selected chimeric proteins, or antibody/cytotoxin or antibody/luminophore conjugates that can be produced using the mammalian vectors of the invention include those that recognise any one or a combination of proteins including, but not limited to, any of the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1a, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β, and analogues thereof, VEGF, TGF, TGF-β2, TGF-p1, EGF receptor VEGF receptor, hepatocyte growth factor, osteoprotegerin ligand, interferon gamma, B lymphocyte stimulator, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, TRAIL receptors 1, 2, 3, and 4, RANK, a RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, MHC I, carcinoembryonic antigen (CEA), alpha-fetoprotein (AFP), tumour necrosis factor (TNF), Fc-γ-1 receptor, HLA-DR 10 beta, HLA-DR antigen, L-selectin, and IFN-γ.

The mammalian vectors of the invention can also be used to produce recombinant fusion proteins comprising any of the above-mentioned proteins or substantially similar proteins. For example, recombinant fusion proteins comprising one of the above-mentioned proteins plus a multimerisation domain, such as a leucine zipper, a coiled coil, an Fc portion of an antibody, or a substantially similar protein, can be produced using the mammalian vectors of the invention. Specifically included among such recombinant fusion proteins are proteins in which at least a portion of TNFR or RANK is fused to an Fc portion of an antibody.

It will be understood that the skilled artisan is fully capable to determine a variety of further proteins which are contemplated to be used in connection with the present invention.

Genetic elements (see the abbreviations utilised in FIG. 1) comprised in the vectors according to the present invention (and in particular in pDGPΔGOI/pDGP) are:

SV40 enh/prom: the simian virus 40 enhancer and early promoter region;

Hbb intronII, or fragments, derivatives and modifications thereof, as defined above.

Genetic elements (see the abbreviations utilised in FIG. 1) that may be comprised in the vectors according to the present invention (and in particular in pDGPΔGOI/pDGP) are:

neo: the aminoglycoside-3'-phosphotransferase (APH 3' II) gene, also named neomycin phosphotransferase gene, from Tn5; APH 3' II inactivates the antibiotic geneticin (G418);

dhfr: the dihydrofolate reductase gene;

SV40 polyA: the polyadenylation signal sequence from SV40;

synth polyA: a synthetic polyadenylation signal based on the polyadenylation signal of the rabbit β-globin gene.

The pDGP vector as one embodiment exemplifying the present invention (for a vector with at least one gene of interest) is schematically depicted in FIG. 1. It contains two GOI expression cassettes each exhibiting basically identical structures and regulatory elements, except that the genes to be expressed are distinct: the light and heavy chain gene, respectively, of a monoclonal antibody (an anti-CD20-antibody), the expression cassettes thus enabling expression of two distinct genes of interest in mammalian cells.

The pDGP-A vector as another embodiment exemplifying the present invention (for a vector with one gene of interest) is schematically depicted in FIG. 3. It contains one GOI expression cassette exhibiting the gene of the darbepoetin alfa (which is a hormone or erythropoietic factor) under the control of the above-described novel and inventive combination of regulatory elements.

Genes of interest typically are cDNA sequences, but may likewise be (genomic) DNA sequences.

As mentioned previously, the vectors according to the present invention (and in particular pDGPΔGOI/pDGP and pDGP-AΔGOI/pDGP-A) may also contain genes/expression cassettes encoding a selection marker. Preferred selection markers are the neomycin phosphotransferase encoded by the neo gene/expression cassette and the dihydrofolate reductase encoded by the dhfr gene/expression cassette. The genes/expression cassettes encoding the selectable markers allow for selection of transfected cells by, e.g., geneticin (G418) and methotrexate (MTX). The neo expression cassette of pDGP contains the neomycin phosphotransferase gene driven by the SV40 enhancer and early promoter region and is further transcriptionally regulated by a synthetic polyadenylation signal sequence (as to be seen in FIG. 1). The neomycin phosphotransferase gene originates from bacteria and is expressed in mammalian cells if under the control of the regulatory elements mentioned above. Quite conversely, the dhfr expression cassette of pDGP contains the dhfr gene driven by the SV40 early promoter region (without enhancer sequence) and is further transcriptionally regulated by the SV40 polyadenylation signal in 3'- to 5'-orientation. The enzyme dihydrofolate reductase (DHFR) is required for the conversion of dihydrofolate to tetrahydrofolate which, in turn, is required for nucleic acid synthesis in cells. Efficient cell selection is achieved by irreversible inhibition of dihydrofolate reductase by methotrexate. Thus, growth of mammalian cells successfully transfected with the pDGP vector (and thus overexpressing the DHFR protein) is enabled in a methotrexate-supplemented growth medium.

FIG. 1 schematically depicts a vector in accordance with a preferred embodiment of the present invention (vector pDGP) including two genes of interest, that is, mAb HC and mAb LC (mAb: monoclonal antibody; HC: heavy chain; LC: light chain).

Figure 2:
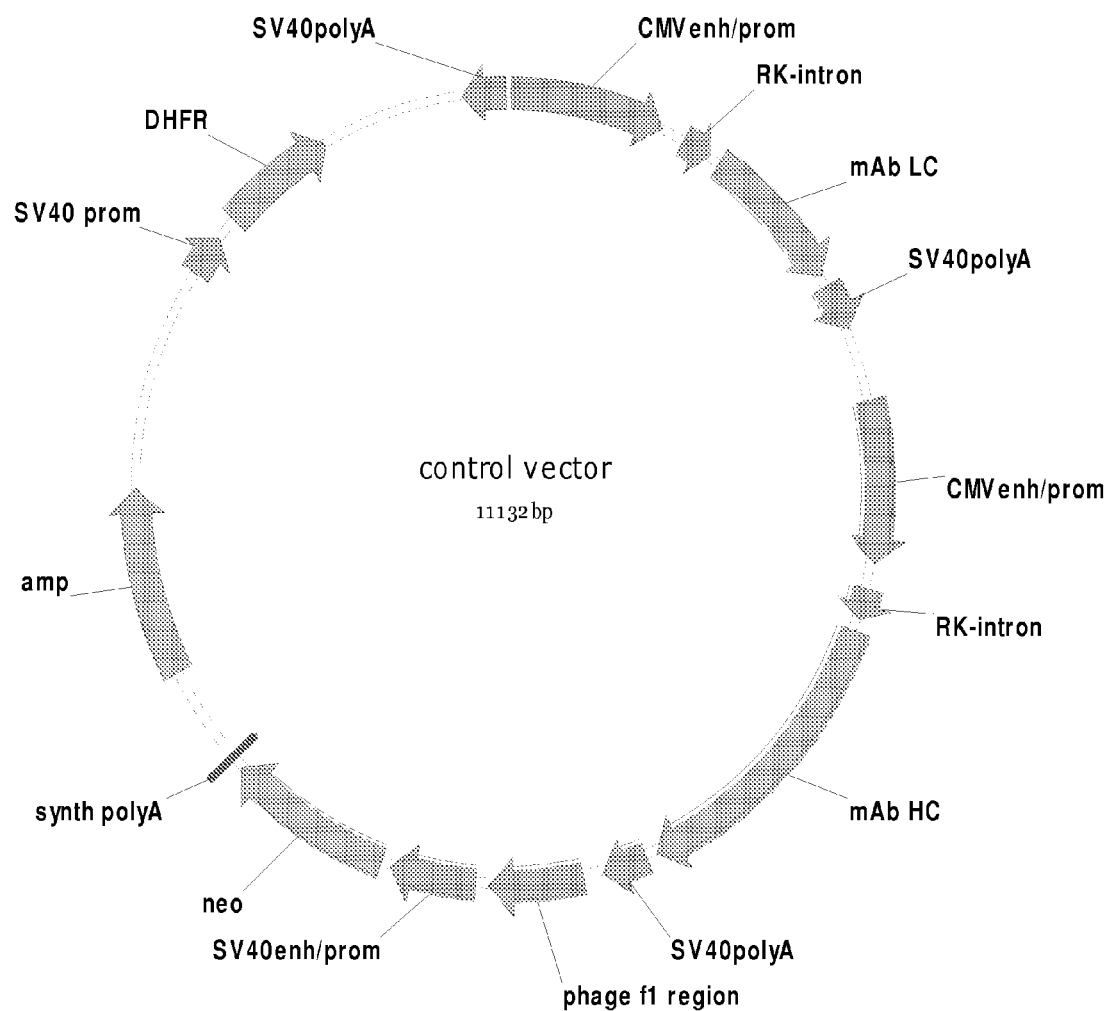

FIG. 2 schematically depicts a control vector.

FIG. 3 schematically depicts a vector in accordance with a preferred embodiment of the present invention (vector pDGP-A) including one gene of interest, that is, darbepoetin alfa (abbreviation: Darbe alfa).

Figure 4:
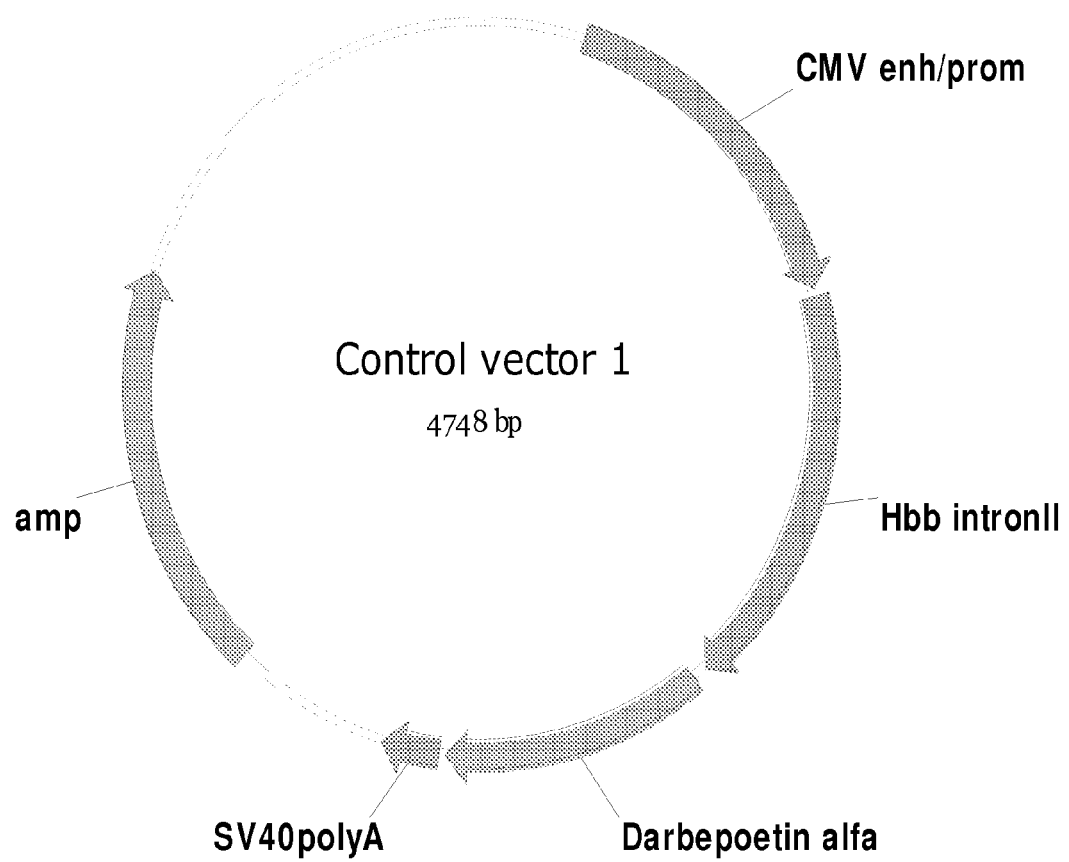

FIG. 4 schematically depicts another control vector, i.e., Control vector 1, wherein the GOI (darbepoetin alfa) expression is under the regulatory control of the CMV enhancer/promoter (CMV enh/prom) and the Hbb intronII.

Figure 5:
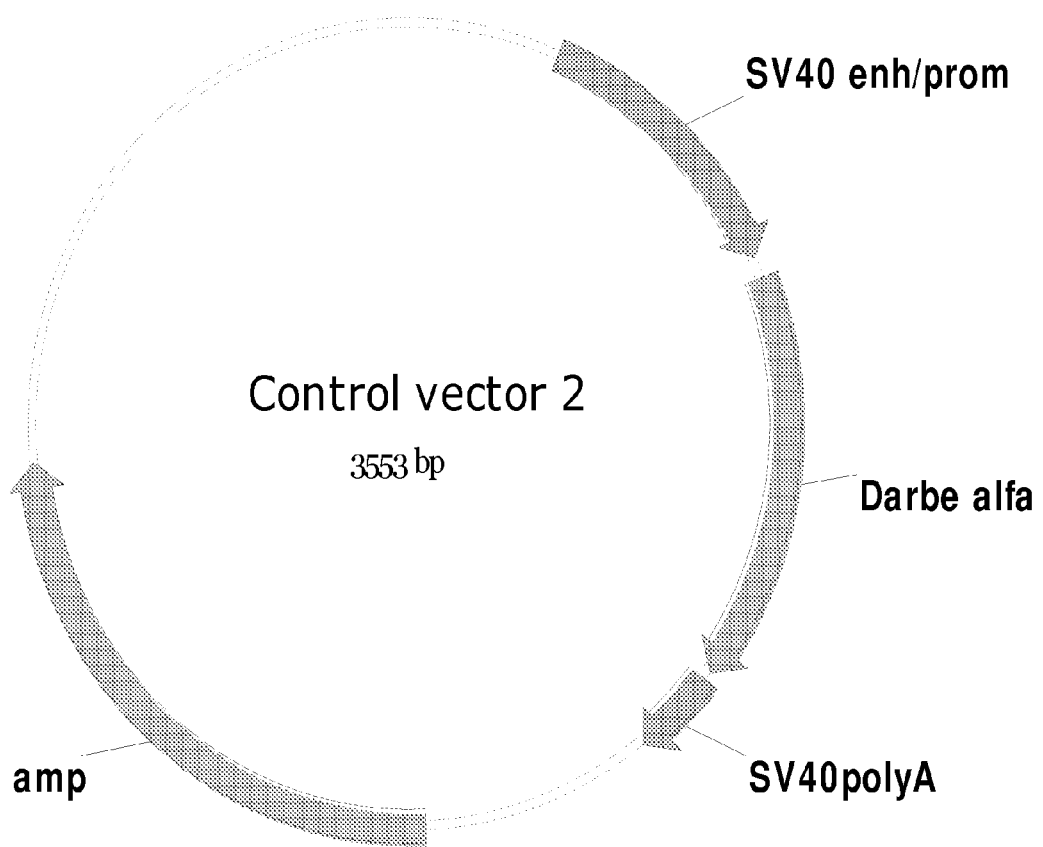

FIG. 5 schematically depicts still another control vector, i.e., Control vector 2, wherein the GOI (darbepoetin alfa) expression is under the regulatory control of the SV40 enhancer/promoter (SV40 enh/prom) only (without any intron sequences).

In an attempt to test the performance of the pDGP expression vector according to the present invention the inventors compared pDGP (depicted in FIG. 1) to the control vector (depicted in FIG. 2). Both the pDGP and the control vector include the same two genes of interest: mAb HC and mAb LC (of an anti-CD20-antibody). Both vectors were transfected into the same host cell lines (e.g., CHO K1PD, COS1, CV1, Vero, HeLa, HEK-293, PER C6). Cells were then subjected to successive selection steps in the presence of G418 and MTX. After each selection step mAb titres in standard shake flask batches were determined and compared. Experimental details are presented below.

In a further attempt to test the performance of the pDGP-A expression vector according to the present invention the inventors compared pDGP-A (depicted in FIG. 3) to Control vector 1 and 2 (depicted in FIGS. 4 and 5, respectively). Both the pDGP-A and Control vector 1 and 2 include the same gene of interest: darbepoetin alfa, a hormone (erythropoietic factor). The vectors were transfected into the same host cell lines (e.g., CHO K1PD, COS1, CV1, Vero, HeLa, HEK-293, PER C6). Contrary to the above-mentioned pDGP vector, each of the expression vectors pDGP-A, Control vector 1 and Control vector 2 comprises a single GOI expression cassette and does not comprise any eukaryotic selection marker gene(s). Therefore, the Neo vector—comprising the neomycin resistance gene—was co-transfected in order to enable the one-step selection in medium containing geneticin (G418). Experimental details are presented below.

EXPERIMENTS

The mammalian vectors according to the invention may be and were used to produce various different (recombinant) proteins. The following examples illustrate the general experimental setting of the recombinant expression of a multimeric and monomeric protein, respectively. In particular, the data presented hereinafter have been collected by using a monoclonal antibody directed against CD20 and darbepoetin alfa, a hormone (erythropoietic factor), as exemplary proteins which can be expressed using the mammalian vector according to the invention.

Example 1

Expression of a Multimeric Protein (Monoclonal Anti-CD20 Antibody)

Expression Vector Design and Construction

Vectors used in this study were designed in silico using vector NTI 9.0 evaluation software. Fragments required for the construction of vectors such as the pDGP vector and the control vector (FIG. 2) were prepared at Geneart AG, Regensburg, Germany. It is understood by those of skill in the art that several vector assemblies according to the teachings of the present invention are feasible. As the individual elements of the vectors according to the invention are known in the art, suitable vectors can be assembled e.g. by sequencing or amplification and appropriate cloning of the basic genetic elements and expression cassettes. Hence, it will be understood that several other embodiments and ways to obtain respective vectors are suitable and readily available.

Regulatory genetic elements driving expression of the 4 expression cassettes in each expression vector are listed in Table 1.

6. Add the mixture from step 5 to a transfection cuvette and place same in an Amaxa Nucleofector device.
7. Transfect the cells using Amaxa program U 23.
8. For cells growing in shake flasks (e.g., CHO K1PD) add some growth medium in the cuvette and transfer the cells carefully to a 125 ml shake flask by utilising 20 ml of the growth medium. Rinse the cuvette once or twice with fresh growth medium and add it to the shake flask. Incubate the cells 24-48 h in a shaker (110 rpm), at 37° C., 10% $CO_2$.

TABLE 1

List of regulatory genetic elements comprised in the pDGP/control vector

| | GOI (2) | | | neo | | dhfr | |
|---|---|---|---|---|---|---|---|
| Vector | promoter | intron | polyA | promoter | polyA | promoter | polyA |
| pDGP vector | SV40 enh/prom | Hbb intronII | SV40 polyA | SV40 enh/prom | synth polyA | SV40 prom | SV40 polyA |
| Control vector | CMV enh/prom | RK-intron | SV40 polyA | SV40 enh/prom | synth polyA | SV40 prom | SV40 polyA |

Vector Preparation for Transfection

Both expression vectors were linearised using single cutter restriction endonuclease SwaI (ATTT AAAT, Roche, Cat. No. 11 371 525 001). A maximum of 100 μg of vector DNA per reaction was digested using SwaI at 5 U/μg DNA. Appropriate amounts of 10× reaction buffer and $H_2O$ were added to the reaction mixtures. Reaction mixtures were incubated at 25° C. 4 h-overnight. After digestion DNA precipitation was performed in a laminar air flow chamber as described below:
  Add 1 volume of isopropanol
  Vortex thoroughly
  Centrifuge 30 min at 21000×g at 4° C.
  Discard the supernatant
  Add carefully 1 volume of sterile, ice cold 70% ethanol
  Centrifuge 1 min at max. speed, at 4° C.
  Discard the supernatant
  Air dry pellet at RT for 5-30 min (in laminar)
  Resuspend DNA in 100 μl sterile water.

After digestion the purity (OD 260/280) and concentration of linear DNA was determined using NanoDrop ND-1000. Gel electrophoresis of digested DNA (0.8% agarose e-gel, Invitrogen) was performed to control the linearization.

Host Cells

CHO K1PD, COS1, CV1, Vero, HeLa, HEK-293, PER C6 cells were used.

The CHO K1PD cell line is a subpopulation of the CHO K1 cell line originating from ATCC (Cat. No. CCL-61.3). The original cell line was adapted to serum-free suspension culture in DM122 medium. DM122 growth medium was used for all experiments employing CHO K1PD cells.

Transfection

The Amaxa system was used for cell transfection (Nucleofector kit V, Cat. No.: VCA-1003). No more than 5 pools are transfected at once, to enable sufficient time for all necessary cell manipulations. The detailed protocol is as follows:
1. At the time of transfection, cells should be up to $2 \times 10^6$/ml with a viability ≥90%.
2. $5 \times 10^6$ cells are used per transfection.
3. Count cells and centrifuge at 90×g, 10 min, RT in a 50 ml centrifuge tube.
4. Carefully remove the medium and resuspend the cell pellet in 100 μl of solution V (contained in the Amaxa kit)
5. Add DNA (3 μg) and mix gently.

Growth Medium and G418/MTX Selection

The cells (e.g. CHO K1PD, COS1, CV1, Vero, HeLa, HEK-293, PER C6 cells) were cultivated in a suitable medium for culturing mammalian cells, such as DM122 growth medium supplemented with 8 mM L-glutamine (Sigma, Cat. No. G7513) when using CHO K1PD for the experiments.

Selection steps were performed in the same medium additionally supplemented with G418 (Geneticin, Gibco, Cat. No. 10131-027; final concentration: 0.8 mg/ml) and/or methotrexate (methotrexate hydrate, Sigma, Cat. No. M8407150; final concentration: 150 or 250 nM). G418 selection was the first selection step after transfection. G418 was added to the cells 2-5 days after transfection when cell viability exceeded 60%. G418 selection usually takes 2-4 weeks. Once cell viability had reached at least 85%, MTX selection was carried out.

A seeding density of $2 \times 10^5$ viable cells per ml was used to start MTX selection on G418 pre-selected cells. Two selection sub-steps were performed using the above indicated MTX concentrations (150/250 nM). MTX selection usually takes 2 to 3 weeks, until cell viability reached more than 85%.

Thawing/Freezing of Cells

The cells were thawed at 37° C. and drop-wise inoculated directly to 250 ml shake flasks containing 50 ml pre-warmed medium at an initial cell density of about $10^5$ viable cells per ml. Cells were cultured at 37° C., 10% $CO_2$, 110 rpm.

Cells were frozen in exponential growth phase at viability >90%. $5\text{-}10 \times 10^6$ viable cells per vial were frozen in conditioned medium containing 7.5% DMSO. First, the cell culture was centrifuged at 180×g, 5 min, RT. Second, the supernatant was partially removed. Then, DMSO was added to the remaining supernatant to a final concentration of 7.5%. Cell pellets were gently resuspended. Cryo-vials were filled with 1 ml of the cell suspension each and transferred into a −80° C. deep freezer in a Mr. Frosty cryo box. Within 1 month the frozen cells in the cryo-vials were transferred into a liquid nitrogen container.

Culture and Handling of Cells

Cells were split every 2-3 days at a density of $1\text{-}1.5 \times 10^5$ viable cells per ml and added to the appropriate pre-warmed growth medium to maintain exponential growth.

Incubation conditions: 37° C., 90-110 rpm (for 125 & 250 ml shake flasks), 10% $CO_2$ (for DM122 medium).

Testing for mAb Expression

After each selection step (G418, MTX) a ten-day batch experiment in appropriately supplemented medium (e.g., DM122) was performed to evaluate the expression of mAb. Cells were seeded at a final density of $1.5 \times 10^5$ viable cells/ml in 125 ml shake flasks. The total culture volumes were 25 ml. Cells were cultivated in a shaking incubator (37° C., 110 rpm, 10% $CO_2$). At day 10, 1 ml cell culture supernatant samples were taken to measure the mAb titre. The mAb content was determined by AC (Affinity Chromatography with Protein A).

Results

Ten-day batch titres of cells transfected with pDGP vector after different selection steps are shown in Table 2.

TABLE 2

Ten-day batch titres; cells transfected with pDGP vector after different selection steps

| Experiment | G418 Titre (mg/l) | 150 nM MTX Titre (mg/l) | 250 nM MTX Titre (mg/l) |
|---|---|---|---|
| 1 | 94 | 246 | 281 |
| 2 | 80 | 249 | 284 |
| 3 | 94 | 225 | 288 |
| 4 | 96 | 229 | 303 |
| 5 | 91 | 218 | 309 |
| 6 | 84 | | |
| 7 | 74 | 212 | 339 |
| 8 | 89 | 216 | 289 |
| 9 | 89 | | |
| 10 | 94 | 243 | 260 |

Ten-day batch titres of cells transfected with control vector after different selection steps are shown in Table 3

TABLE 3

Ten-day batch titres; cells transfected with control vector after different selection steps

| Experiment | G418 Titre (mg/l) | 150 nM MTX Titre (mg/l) | 250 nM MTX Titre (mg/l) |
|---|---|---|---|
| 1 | 15 | 190 | 192 |
| 2 | 15 | 247 | 372 |
| 3 | 14 | 251 | 219 |
| 4 | 15 | 207 | 341 |
| 5 | 15 | 154 | 385 |
| 6 | 15 | 422 | 646 |

Compared to the cells transfected with the control vector, 4-5 times higher titres were measured for cells transfected with pDGP after G418 selection. In average, the same titres were measured for both experimental approaches after MTX selection. However, the achieved titres were much more reproducible with the cells transfected with pDGP (±10%) compared to the cells transfected with control vector (±50%).

Example 2

Expression of a Monomeric Protein (Darbepoetin Alfa)

Expression Vector Design and Construction

Vectors and fragments used in this study were designed and prepared as described in Example 1. The expression experiments with darbepoetin alfa were performed using a further derivative of the above-mentioned pDGPΔGOI vector, the pDGP-AΔGOI vector. The pDGP-AΔGOI vector comprises the same novel and inventive combination of regulatory elements driving GOI expression, when inserted, as the aforementioned pDGPΔGOI vector (and the pDGP vector of Example 1): the simian virus 40 enhancer and early promoter region and the Hbb intronII. In the present example, darbepoetin alfa is inserted into pDGP-AΔGOI as an exemplary protein of interest. In addition, Control vector 1, Control vector 2, and the Neo vector were used in this study (see below).

Contrary to the pDGP vector used in Example 1, each of the above mentioned expression vectors (except for the Neo vector) comprises a single GOI expression cassette and does not comprise any eukaryotic selection marker gene(s). Therefore, the Neo vector—comprising the neomycin resistance gene— was co-transfected in all experiments in order to enable the selection in medium containing geneticin (G418). Example 2 thus represents a vector system according to the third aspect of the invention.

The regulatory genetic elements driving the expression of darbepoetin alfa in the pDGP-A vector and in Control vector 1 and 2 are listed in Table 4. Table 4 likewise shows the regulatory genetic elements driving the expression of the neomycin resistance gene in the Neo vector.

TABLE 4

List of genetic regulatory elements comprised in the pDGP-A vector, Control vector 1, Control vector 2 and Neo vector

| Vector | GOI (darbepoetin alfa) | | | neo | |
| | promoter | intron | polyA | promoter | polyA |
|---|---|---|---|---|---|
| pDGP-A | SV40 enh/prom | Hbb intronII | SV40 polyA | — | — |
| Control vector 1 | CMV enh/prom | Hbb intronII | SV40 polyA | — | — |
| Control vector 2 | SV40 enh/prom | — | SV40 polyA | — | — |
| Neo vector | — | — | — | SV40 enh/prom | SV40 polyA |

Host Cells

The same cell lines as in Example 1 were used.

Transfection

The same transfection method and system were used as in Example 1.

Growth Medium and G418 Selection

The cells (e.g. CHO K1PD, COS1, CV1, Vero, HeLa, HEK-293, PER C6 cells) were cultivated in a suitable medium for culturing mammalian cells, such as the in-house developed DM122 growth medium supplemented with 8 mM L-glutamine (Sigma, Cat. No. G7513) when using CHO K1PD for the experiments.

The selection step was performed in the same medium additionally supplemented with G418 (Geneticin, Gibco, Cat. No. 10131-027; final concentration: 0.8 mg/ml).

G418 was added to the cells 2-5 days after transfection when cell viability exceeded 60%. G418 selection usually takes 2-4 weeks.

Thawing/Freezing of Cells

The thawing/freezing of cells was performed as described in Example 1.

Culture and Handling of Cells

The culturing and handling of cells was performed as described in Example 1.

Testing for Darbepoetin Alfa Expression

Pools were tested for stable darbepoetin alfa expression after the G418 selection step. A batch experiment in appropriately supplemented medium (e.g., DM122) was performed to evaluate the expression of darbepoetin alfa. Cells were seeded at a final density of 1.5×10⁵ viable cells/ml in 125 ml shake flasks. The total culture volumes were 25 ml. Cells were cultivated in a shaking incubator (37° C., 110 rpm, 10% $CO_2$). At days 5 and 9, 0.5 ml cell culture supernatant samples were taken to measure the darbepoetin alfa titre. The darbepoetin alfa content was determined by an EPO-specific ELISA (Enzyme-Linked ImmunoSorbent Assay) test (Epo-ELISA Quantikine kit, R&D Systems, Cat. No.: DEP00).

Results

Darbepoetin alfa contents on days 5 and 9 in batch cultures of cells transfected with pDGP-A, control vector 1, and control vector 2 are shown in Table 5.

TABLE 5

Darbepoetin alfa content on days 5 and 9 in batch cultures of cells transfected with the pDGP-A vector, Control vector 1, and Control vector 2, respectively.

| Experiment | Day 5 Titre (mg/l) | Day 9 Titre (mg/l) |
| --- | --- | --- |
| pDGP-A | | |
| 1 | 27.4 | 76.4 |
| 2 | 26.9 | 49.1 |
| Control vector 1 | | |
| 1 | 3.7 | 8.4 |
| 2 | 5.0 | 8.3 |
| Control vector 2 | | |
| 1 | 1.9 | 5.5 |
| 2 | 1.7 | 4.2 |

Compared to the cells transfected with Control vector 1, 5 to 10 times higher titres were obtained from cells transfected with the pDGP-A vector after G418 selection. Compared to the cells transfected with Control vector 2, the use of the pDGP-A vector resulted in an up to 14 times higher titre of darbepoetin alfa, showing the advantage and superiority of the combination of simian virus 40 enhancer and early promoter region and Hbb intronII as regulatory elements to drive recombinant protein expression.

CONCLUSION

The expression vectors of the present invention (such as pDGP and pDGP-A) provide the following advantages over expression vectors currently used in the art (such as the control vectors):

Due to high reproducibility, the use of pDGP and pDGP-A, as examples of the vectors according to the invention, considerably reduces the number of cell samples (i.e., transfected cell pools) to be generated and tested to only 3 to 5, thereby reducing the work load significantly. Currently, the generation of a high number of cell samples (up to 50) due to low reproducibility is generally required to identify high producing cell samples.

The use of vectors such as pDGP and pDGP-A provides adequate titres of the expressed protein of interest for product characterisation, preclinical and phase I studies after just one single G418 selection step. Additional MTX selection steps to increase the protein (e.g., antibody) titre prior to cell cloning are not required.

The time required to develop a cell line can be remarkably reduced when using, e.g., pDGP or pDGP-A, as the number of selection steps is reduced to one G418 step only.

REFERENCES

1 Trill J J, Shatzman A R, Ganguly S: Production of monoclonal antibodies in COS and CHO cells. Current Opinion in Biotechnology 6, 1995: 553-560

2 Xu Z, Mizuguchi H, Ishii-Watabe A, Uchida E, Mayumi T, Hayakawa T: Optimization of transcriptional regulatory elements for constructing plasmid vectors. Gene 272, 2006: 149-156

3 Melcher R, Grosch H W, Hasilik A: Plasmid vectors with a 5'-hybrid intron facilitate high-level glycoprotein expression in CHO-cells. Biochimica et Biophysica Acta, 1575, 2002: 49-53

4 Kim Y, Kim S, Lee J, Shin, H: Expression vector for mammal comprising murine cytomegalovirus immediate early gene enhancer/promoter and human beta globin intron, cell transformed therewith and method for producing heterologous protein using said cell. Patent: KR 1020000070503-A 2 24 Nov. 2000

5. Xu Z, Mizuguchi H, Ishii-Watabe A, Uchida E, Mayumi T, Hayakawa T: Strength evaluation of transcriptional regulatory elements for transgene expression by adenovirus vector. Journal of Controlled Release, 81, 2002: 155-163

6 Komiya E, Kondoh M, Mizuguchi H, Fujii M, Utoguchi N, Nakanishi T, Watanabe Y: Characteristics of Transcription-regulatory Elements for Gene Expression from Plasmid Vectors in Human Trophoblast Cell Lines. Placenta, 27, 2006: 934-938

The invention claimed is:

1. A mammalian expression vector comprising the following regulatory elements:
    (a) a simian virus 40 enhancer and early promoter region;
    (b) human Hbb intronII; and
    (c) at least one gene encoding a polypeptide of interest,
wherein the human Hbb intron II is located between (i) the simian 40 virus enhancer and early promoter region and (ii) the at least one gene encoding a polypeptide of interest.

2. The vector of claim 1, wherein the human Hbb intron II comprises the sequence of SEQ ID NO:1.

3. The vector of claim 1, wherein the vector further comprises at least one gene encoding a eukaryotic and/or prokaryotic selection marker.

4. The vector of claim 3, wherein the order of the regulatory elements, the at least one gene encoding the polypeptide of interest and the gene encoding a eukaryotic and/or prokaryotic selection marker is as follows:
    (i) 5'-SV40 enhancer/early promoter region, Hbb intron II, gene encoding the light chain of an immunoglobulin, SV40 polyadenylation signal sequence;
    (ii) SV40 enhancer/early promoter region, Hbb intron II, gene encoding the heavy chain of an immunoglobulin, SV40 polyadenylation signal sequence;
    (iii) SV40 enhancer/early promoter region, Tn5 neomycin phosphotransferase gene, a synthetic polyadenylation signal sequence;
    (iv) SV40 early promoter, dihydrofolate reductase gene, SV40 polyadenylation signal sequence-3'.

5. The vector of claim 3, wherein the at least one eukaryotic selection marker gene is the neomycin phosphotransferase gene from Tn5 and/or the dihydrofolate reductase gene.

6. The vector of claim 1, wherein the vector is circular and/or the at least one gene encoding the polypeptide of interest is under the control of (a) and (b).

7. The vector of claim 6, wherein the at least one gene encoding the polypeptide of interest encodes an immunoglobulin light chain and/or an immunoglobulin heavy chain.

8. The vector of claim 1, wherein the vector is the pDGP-ΔGOI vector exhibiting a 9555 bp sequence, one strand of which being represented by SEQ ID NO:2.

9. The vector of claim 8, wherein the vector is circular.

10. A vector system comprising at least two of the expression vector of claim 1.

11. The vector system of claim 10, wherein a first gene encoding a first polypeptide of interest located on a first vector encodes the light chain of an immunoglobulin, and a second gene encoding a second polypeptide of interest located on a second vector encodes the heavy chain of an immunoglobulin.

12. The vector system of claim 10, wherein a first vector comprises the at least one gene encoding the polypeptide of interest, and wherein a second vector comprises at least one gene encoding a selection marker conferring resistance to a transfected cell.

13. The vector system of claim 10, wherein a first vector is the pDGP-AΔGOI vector exhibiting a 3830 bp sequence, one strand of which being represented by SEQ ID NO:3.

14. An isolated mammalian cell comprising the expression vector of claim 1.

15. The cell of claim 14, wherein the cell is selected from the group consisting of: a COP cell, an L cell, a C127 cell, an Sp2/0 cell, an NS-0 cell, an NIH3T3 cell, a PC12 cell, a PC12h cell, a BHK cell, a CHO cell, a COS1 cell, a COS3 cell, a COST cell, a CV1 cell, a Vero cell, a HeLa cell, an HEK-293 cell, a PER C6 cell, a cell derived from diploid fibroblasts, myeloma cells, and HepG2.

16. An ex vivo-method for producing a cell comprising an expression vector comprising contacting a mammalian cell with the mammalian expression vector of claim 1.

17. A method for producing at least one polypeptide of interest comprising culturing a cell comprising the mammalian expression vector of claim 1 in a cell culture medium under conditions allowing expression of said at least one polypeptide of interest.

18. The method of claim 17, wherein said at least one polypeptide of interest is/are secreted into the cell culture medium and said method further comprises the step of isolating from the cell culture medium said at least one polypeptide of interest.

19. An isolated mammalian cell comprising the vector system of claim 10.

20. An ex vivo-method for producing a cell comprising a vector system comprising contacting a mammalian cell with the vector system of claim 10.

* * * * *